United States Patent [19]

Matsumoto et al.

[11] Patent Number: 4,642,313

[45] Date of Patent: * Feb. 10, 1987

[54] FURYLOXAZOLYLACETIC ACID DERIVATIVES AND PROCESSES FOR PREPARING SAME

[75] Inventors: Kazuo Matsumoto, Ibaraki; Kohki Takashima, Tokyo, both of Japan

[73] Assignee: Tanabe Seiyaku Co., Ltd., Osaka, Japan

[ * ] Notice: The portion of the term of this patent subsequent to Jul. 17, 2001 has been disclaimed.

[21] Appl. No.: 465,544

[22] Filed: Feb. 10, 1983

[30] Foreign Application Priority Data

Feb. 26, 1982 [JP] Japan ................... 57-30921

[51] Int. Cl.$^4$ .................. C07D 263/30; A61K 31/42
[52] U.S. Cl. .................. 514/374; 548/236
[58] Field of Search ............... 424/272; 548/236, 204

[56] References Cited

U.S. PATENT DOCUMENTS

| 3,506,679 | 4/1970 | Cavalla et al. | 548/204 |
| 3,579,529 | 5/1971 | Brown et al. | 548/236 |
| 4,365,066 | 12/1982 | Yamanaka et al. | 424/272 |
| 4,460,596 | 7/1984 | Matsamoto et al. | 514/374 |

FOREIGN PATENT DOCUMENTS

| 2068418 | 10/1969 | France | 424/272 |
| 1542315 | 3/1979 | United Kingdom | 548/236 |

OTHER PUBLICATIONS

Burger, Alfred, *Medicinal Chemistry (III)* Wiley-Interscience, New York (1970) p. 956.

*Primary Examiner*—Glenna M. Hendricks
*Attorney, Agent, or Firm*—Birch, Stewart, Kolasch & Birch

[57] ABSTRACT

A furyloxazolylacetic acid derivative of the formula:

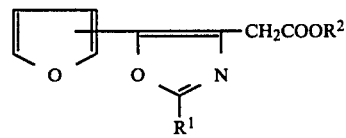

wherein $R^1$ is alkyl of one to 6 carbon atoms, cycloalkyl of 5 to 6 carbon atoms, phenyl or a substituted phenyl (said substituted phenyl being phenyl group substituted with one or two radicals selected from alkyl of one to 2 carbon atoms, alkoxy of one to 2 carbon atoms and halogen), and $R^2$ is hydrogen or alkyl of one to 12 carbon atoms. The compound (I) is useful as a hypolipidemic agent.

17 Claims, No Drawings

FURYLOXAZOLYLACETIC ACID DERIVATIVES AND PROCESSES FOR PREPARING SAME

This invention relates to a furyloxazolylacetic acid derivative and processes for preparing same. More particularly, it relates to a furyloxazolylacetic acid derivative of the formula:

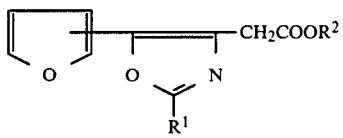

wherein $R^1$ is alkyl of one to 6 carbon atoms, cycloalkyl of 5 to 6 carbon atoms, phenyl or a substituted phenyl (said substituted phenyl being phenyl group substituted with one or two radicals selected from alkyl of one to 2 carbon atoms, alkoxy of one to 2 carbon atoms and halogen), and $R^2$ is hydrogen or alkyl of one to 12 carbon atoms.

The compound (I) in which $R^2$ is hydrogen can exist in the form of either a free acid or a pharmaceutically acceptable salt thereof, and the present invention also includes within its scope such pharmaceutically acceptable salt of the compound (I).

Hyperlipidemia is known to be one of the important causative factors of arteriosclerosis, and various compounds such as dextran sulfate, simfibrate (chemical name: 2-(4-chlorophenoxy)-2-methylpropanoic acid 1,3-propanediyl ester), nicomol (chemical name: nicotinic acid 1,1,3,3-tetraester with 2-hydroxy-1,1,3,3-cyclohexanetetramethanol), clofibrate (chemical name: 2-(4-chlorophenoxy)-2-methylpropanoic acid ethyl ester) and vitamin E nicotinate have been used for the treatment or prophylaxis of said hyperlipidemia.

As a result of investigations, it has now been found that the furyloxazolylacetic acid derivative (I) of the present invention is useful as a hypolipidemic agent. In particular, the furyloxazolylacetic acid derivative (I) shows potent hypolipidemic activity without undesirable side effects such as hepatic disfunction. Further, the furyloxazolylacetic acid derivative (I) also shows a potent platelet aggregation-inhibiting activity.

Representative examples of the furyloxazolylacetic acid derivative include those of the formula (I) in which the furyl group is 2-furyl or 3-furyl; $R^1$ is alkyl of one to 6 carbon atoms (e.g., methyl, ethyl, propyl, isopropyl, butyl, isobutyl, pentyl, isopentyl, hexyl), cycloalkyl of 5 to 6 carbon atoms (e.g., cyclopentyl, cyclohexyl) or phenyl; or $R^1$ is phenyl substituted with one to 2 radicals selected from alkyl of one to 2 carbon atoms (e.g., methyl, ethyl), alkoxy of one to 2 carbon atoms (e.g., methoxy, ethoxy) and halogen atoms (e.g., chlorine, fluorine, bromine, iodine); and $R^2$ is hydrogen or alkyl of one to 12 carbon atoms (e.g., methyl, ethyl, propyl, isopropyl, butyl, isobutyl, pentyl, hexyl, heptyl, octyl, lauryl). Among them, a preferred subgenus is the compound of the formula (I) in which $R^1$ is alkyl of one to 4 carbon atoms, cyclohexyl, phenyl, methylphenyl, methoxyphenyl, chlorophenyl, fluorophenyl or dichlorophenyl. Another preferred subgenus is the compound of the formula (I) in which $R^1$ is n-butyl, 4-chlorophenyl, 4-fluorophenyl or 3,4-dichlorophenyl, and $R^2$ is hydrogen or alkyl of one to 4 carbon atoms. A further preferred subgenus is the compound of the formula (I) in which $R^1$ is 4-chlorophenyl, 4-fluorophenyl or 3,4-dichlorophenyl, and $R^2$ is hydrogen or ethyl.

According to the present invention, the compound (I) in which $R^2$ is alkyl of one to 12 carbon atoms is prepared by subjecting a 3-acylaminopropionate derivative of the formula:

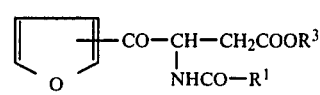

wherein $R^3$ is alkyl of one to 12 carbon atoms and $R^1$ is the same as defined above, to dehydrative cyclization to give a furyloxazolylacetate derivative of the formula:

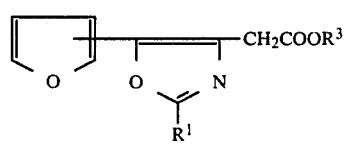

wherein $R^1$ and $R^3$ are the same as defined above.

On the other hand, the compound (I) in which $R^2$ is hydrogen is prepared by hydrolyzing the compound (I-a) obtained above to give a furyloxazolylacetic acid derivative of the formula:

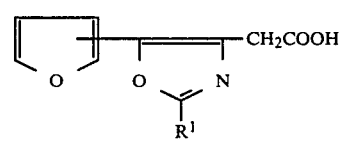

wherein $R^1$ is the same as defined above.

The compound (I) in which $R^2$ is alkyl of one to 12 carbon atoms may also be prepared by subjecting the compound (I-b) obtained above to esterification to give a furyloxazolylacetate derivative of the formula:

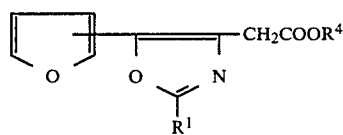

wherein $R^4$ is alkyl of one to 12 carbon atoms.

The dehydrative cyclization of the compound (II) is accomplished in a solvent in the presence of a dehydrating agent. The dehydrating agent includes, for example, phosphorus oxychloride, phosphorus trichloride, phosphorus pentachloride, thionyl chloride, oxalyl chloride, phosgene and phosphorus pentoxide. p-Toluenesulfonic acid and sulfuric acid are also used in a catalytical amount as the dehydrating agent. Chloroform, methylene chloride, carbon tetrachloride, benzene, toluene, xylene, tetrahydrofuran and dimethylformamide are suitable as the solvent. It is preferred to carry out the reaction at a temperature of −5° to 130° C., especially at a temperature of −5° to 60° C.

The hydrolysis of the compound (I-a) is accomplished by treating said compound with an acid or an alkali agent in a solvent. The acid includes, for example, mineral acids such as hydrochloric acid or sulfuric acid. On the other hand, the alkali agent includes, for example, alkali metal hydroxides such as sodium hydroxide or potassium hydroxide. Water, alkanol (e.g., methanol, ethanol, propanol), tetrahydrofuran, dioxane and a mixture thereof are suitable as the solvent. It is preferred to carry out the reaction at a temperature of 0° to 100° C., especially at a temperature of 10° to 30° C.

The esterification of the compound (I-b) is accomplished by reacting a reactive derivative of said compound with an alkanol of the formula: $R^4$—OH (wherein $R^4$ is the same as defined above). The reactive derivative of the compound (I-b) includes, for example, the corresponding acid halide (e.g., chloride, bromide) and mixed anhydride (e.g., ethoxycarbonyl ester, isobutyloxycarbonyl ester). Especially, it is preferred to use the acid halide as the reactive derivative of the compound (I-b). On the other hand, the alkanol ($R^4$—OH) includes, for example, methanol, ethanol, propanol, isopropanol, butanol, isobutanol, pentanol, isopentanol, octanol and lauryl alcohol. When the acid halide of the compound (I-b) is used, the esterification is conducted in a solvent in the presence or absence of an acid acceptor. The acid acceptor includes, for example, triethylamine, tributylamine, pyridine, sodium carbonate, potassium carbonate and sodium bicarbonate. Methylene chloride, chloroform, carbon tetrachloride, ethyl acetate, tetrahydrofuran, dioxane, acetonitrile, benzene, toluene and dimethylformamide are suitable as the solvent. When an excess of the alkanol ($R^4$—OH) is used, it is not always necessary to use the solvent because said alkanol serves as the solvent. It is preferred to carry out the reaction at a temperature of $-10°$ to 60° C., especially at a temperature of $-10°$ to 30° C. Concomitantly, the acid halide of the compound (I-b) which is used in the above-mentioned reaction is prepared by reacting the compound (I-b) or its salt (e.g., sodium salt, potassium salt, triethylamine salt, tributylamine salt) with a halogenating agent in a solvent. The halogenating agent includes, for example, thionyl chloride, oxalyl chloride, phosphorus oxychloride, phosphorus trichloride, phosphorus tribromide and phosphorus pentachloride. Benzene, toluene, chloroform, tetrahydrofuran and acetonitrile are suitable as the solvent. When an excess of the halogenating agent is used, it is not always necessary to use the solvent because said halogenating agent serves as the solvent. It is preferred to carry out the halogenation reaction at a temperature of $-10°$ to 60° C.

Alternatively, the esterification of the compound (I-b) may be conducted by reacting said compound with the alkanol ($R^4$—OH) in a solvent in the presence of a dehydrating agent and an acid acceptor. The dehydrating agent includes, for example, 2-chloro-1-methylpyridinium iodide and 2-bromo-1-methylpyridinium iodide. On the other hand, the acid acceptor includes, for example, triethylamine, tributylamine and pyridine. Tetrahydrofuran, dioxane, acetonitrile, toluene, benzene and chloroform are suitable as the solvent. It is preferred to carry out the reaction at a temperature of 0° to 30° C.

Further, the esterification of the compound (I-b) may be conducted by reacting said compound with the alkanol ($R^4$—OH) in the presence of an acid. p-Toluenesulfonic acid and sulfuric acid are suitable as the acid. It is preferred to carry out the reaction at a temperature of 50° to 100° C.

Furthermore, the esterification of the compound (I-b) may be conducted by reacting said compound with an alkyl halide of the formula: $R^4$—X (wherein X is halogen and $R^4$ is the same as defined above) in a solvent in the presence of an acid acceptor. The alkyl halide ($R^4$—X) includes, for example, methyl iodide, ethyl iodide, propyl bromide, butyl bromide, pentyl chloride and lauryl bromide. The acid acceptor includes, for example, potassium carbonate, sodium carbonate, triethylamine and tributylamine. Tetrahydrofuran, dioxane, chloroform, benzene, toluene, ethyl acetate and dimethylformamide are suitable as the solvent. It is preferred to carry out the reaction at a temperature of 10° to 100° C.

The compound (I) ($R^2$=H) of the present invention can be used for pharmaceutical use in the form of either free acid or a pharmaceutically acceptable salt thereof. Pharmaceutically acceptable salts of the compound (I) ($R^2$=H) include, for example, alkali metal salts such as sodium and potassium salts; alkaline earth metal salts such as calcium and magnesium salts; salts thereof with amino acids such as lysine, ornithine, arginine and histidine salts; and ammonium salt. Such pharmaceutically acceptable salts may be prepared, for example, by neutrallizing the free acid with a stoichiometrically equimolar amount of a base such as an alkali metal hydroxide, an alkaline earth metal hydroxide, ammonia or a basic amino acid. The compound (I) and a salt thereof can be administered either orally or parenterally. For oral administration, the compound (I) or a salt thereof may be used in the form of tablets, powder, capsules, granules and the like. Known medicinal excipients such as calcium carbonate, calcium phosphate, corn starch, potato starch, sugar, lactose, talc, magnesium stearate and so forth may be used in making these pharmaceutical preparations. Alternatively, the compound (I) or a salt thereof may be used for oral administration in the form of aqueous or oily suspensions, solutions, syrups or elixirs. On the other hand, injections and suppositories are suitable for parenteral administration of the compound (I) or its salts, and said injections may be made in the form of solutions or suspensions, if required, in conjunction or admixture with distilled water, essential oil (e.g., peanut oil, corn oil) or non-aqueous solvent (e.g., polyethyleneglycol, polypropyleneglycol, lanoline, coconut oil). The daily dose of the compound (I) or a salt thereof may vary depending on the administration route, the age, weight or conditions of patients, and the severity of diseases to be treated. In general, however, a preferred dose of said compound (I) or a salt thereof may be 0.1 to 50 mg, especially 5 to 20 mg, per kilogram of body weight per day.

Concomitantly, the starting compound (II) of the present invention is a novel compound and can be prepared, for example, according to the method shown in the following reaction scheme:

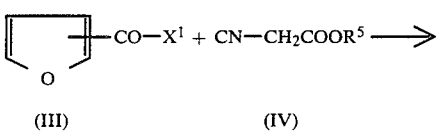

(III)        (IV)

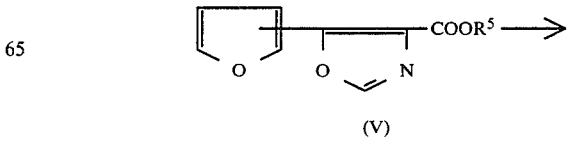

(V)

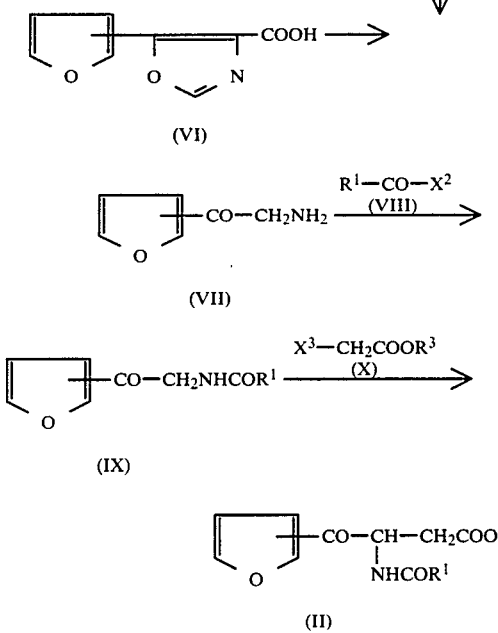

wherein $R^5$ is lower alkyl, $X^1$ is halogen atom or a group of the formula:

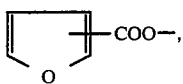

$X^2$ and $X^3$ are halogen atom, and $R^1$ and $R^3$ are the same as defined above.

The reaction of the 2- or 3-furancarboxylic acid derivative (III) with the isocyanoacetate compound (IV) is carried out in a solvent (e.g., tetrahydrofuran, dioxane, dimethylformamide) in the presence of a base such as triethylamine, potassium t-butoxide or 1,8-diazabicyclo[5.4.0]undecene-7 at $-50°$ to $50°$ C. The oxazole derivative (V) thus obtained is saponified with an alkali metal hydroxide (e.g., sodium hydroxide, potassium hydroxide) at $20°$ to $50°$ C., and the reaction mixture is acidified to give the oxazolecarboxylic acid derivative (VI) which is then treated with a mineral acid (e.g., 2N hydrochloric acid-methanol) at $40°$ to $80°$ C. to give the aminoketone compound (VII). Alternatively, the aminoketone compound (VII) may also be prepared by hydrolyzing the compound (V) with a mineral acid, for example, by treating the compound (V) with 4N hydrochloric acid at $50°$ to $80°$ C. The subsequent reaction of the aminoketone compound (VII) with the acid halide (VIII) is carried out in a solvent (e.g., ethyl acetate, benzene) in the presence of an acid acceptor (e.g., sodium hydroxide, sodium bicarbonate) at $-20°$ to $20°$ C. The N-acylamine derivative (IX) thus obtained is then reacted with the halogenoacetate compound (X) in a solvent (e.g., tetrahydrofuran, dioxane, dimethylformamide, dimethylsulfoxide, acetonitrile) in the presence of an acid acceptor (e.g., sodium hydroxide, potassium t-butoxide, n-butyl lithium) at $-50°$ to $30°$ C. to give the 3-acylaminopropionate derivative (II).

Practical and presently-preferred embodiments of the present invention are illustratively shown in the following lines.

EXPERIMENT 1

(Hypolipidemic activity)

A test compound (50 mg %) was added to a commercial diet, and male SD rats (body weight: 120–140 g, a group of 5 rats) were fed with the diet ad libitum for one week. After the experimental period, blood was collected from the tail vein of the rats under ether anesthesia. Then, the liver was excised from the rats and the weight thereof was measured. On the other hand, serum cholesterol and serum triglyceride were measured according to the methods of Zak (Amr. J. Clin, Pathol., Vol. 24, page 1307 (1954)) and Van Handel-Silversmit (J. Lab. & Clin. Med., Vol. 50, page 152 (1957)), respectively. Based on the results obtained above, the decrease (%) in serum cholesterol or triglyceride and the increase (%) in liver weight were calculated by the following formulae:

$$\text{Decrease (\%) in serum cholesterol or triglyceride} = \left(1 - \frac{\text{Serum cholesterol or triglyceride (mg/ml) in the medicated group}}{\text{Serum cholesterol or triglyceride (mg/ml) in the control group}}\right) \times 100$$

$$\text{Increase (\%) in liver weight} = \left(\frac{\text{Liver weight in the medicated group}}{\text{Liver weight in the control group}} - 1\right) \times 100$$

(Results)

The results are shown in the following Table 1. Concomitantly, each of the test compounds of the present invention showed no substantial increase in liver weight, whereas clofibrate showed 12% increase in liver weight.

TABLE 1

| Test compound | Decrease (%) in serum cholesterol | Decrease (%) in serum triglyceride |
|---|---|---|
| (The compounds of the present invention) | | |
| 2-[2-(4-chlorophenyl)-5-(2-furyl)-4-oxazolyl]-acetic acid | 20 | 35 |
| Ethyl 2-[2-(4-fluorophenyl)-5-(2-furyl)-4-oxazolyl]-acetate | 20 | 24 |
| Ethyl 2-[2-(4-chlorophenyl)-5-(2-furyl)-4-oxazolyl]-acetate | 18 | 47 |
| n-Butyl 2-[2-(4-chlorophenyl)-5-(2-furyl)-4-oxazolyl]acetate | 20 | 27 |
| 2-[2-n-butyl-5-(2-furyl)-4-oxazolyl]acetic acid | 32 | 22 |
| Ethyl 2-[2-(4-chlorophenyl)-5-(3-furyl)-4-oxazolyl]-acetate | 25 | 42 |
| Ethyl 2-[2-(3,4-dichlorophenyl)-5-(3-furyl)-4-oxazolyl]acetate | 19 | 49 |
| Ethyl 2-[2-(4-fluorophenyl)-5-(3-furyl)-4-oxazolyl]-acetate | 30 | 26 |
| 2-[2-(4-chlorophenyl)- | 23 | 42 |

TABLE 1-continued

| Test compound | Decrease (%) in serum cholesterol | Decrease (%) in serum triglyceride |
|---|---|---|
| 5-(3-furyl)-4-oxazolyl]-acetic acid | | |
| 2-[2-(3,4-dichlorophenyl)-5-(3-furyl)-4-oxazolyl]-acetic acid | 19 | 60 |
| 2-[2-(4-fluorophenyl)-5-(3-furyl)-4-oxazolyl]-acetic acid | 23 | 38 |
| (Positive control) Clofibrate | 15 | 16 |

EXPERIMENT 2

(Platelet aggregation-inhibiting activity)

Blood was collected from the abdominal aorta of male SD rats (body weight: 250–300 g) which were anesthetized with ether. Nine volumes of said blood were mixed with one volume of an aqueous 3.8% (w/v) trisodium citrate solution, and the mixture was centrifuged at 500×g for 5 minutes to give platelet-rich plasma (hereinafter referred to as "PRP") as the supernatant solution. The bottom layer was further centrifuged at 1000×g for 10 minutes to give platelet-poor plasma (hereinafter referred to as "PPP") as the supernatant solution. PRP was diluted with PPP so that the blood platelet count was $8-10 \times 10^5/\text{mm}^3$. Then, a mixture of 200 μl of said diluted PRP and 25 μl of a test compound solution (final concentration: 100 μg/ml) was introduced into a glass cell of SIENCO aggregometer (Sienco Inc., Morrison, Colo. Model DP-247-D). After the mixture was stirred at 1100 rpm at 37° C. for 2 minutes, 25 μl of a collagen solution (prepared by Holmsen's method described in Biochim. Biophys. Acta, Vol. 186, page 254 (1969)) was added thereto, and the percentage inhibition of platelet aggregation was calculated in accordance with the following formula from the degree of the platelet aggregation which was estimated by Born's method (Nature, 194, page 927 (1969)).

$$\text{Percentage inhibition of platelet aggregation} = \left(1 - \frac{\text{Degree of platelet aggregation which was estimated by adding test compound}}{\text{Degree of platelet aggregation which was estimated without adding test compound}}\right) \times 100$$

Further, on the basis of said percentage inhibition calculated above, the platelet aggregation-inhibiting activity of the test compound was expressed as (−) if the test compound showed less than 10% inhibition of platelet aggregation; or (+) if the test compound showed not less than 10% inhibition of platelet aggregation.

(Results)

The results are shown in the following Table 2.

TABLE 2

| Test compounds | Platelet aggregation-inhibiting activity |
|---|---|
| (The compounds of the present invention) | |
| 2-[2-(4-chlorophenyl)-5-(2-furyl)-4-oxazolyl]-acetic acid | + |
| Ethyl 2-[2-(4-fluorophenyl)-5-(2-furyl)-4-oxazolyl]-acetate | + |
| Ethyl 2-[2-(4-chlorophenyl)-5-(2-furyl)-4-oxazolyl]-acetate | + |
| Ethyl 2-[2-(4-chlorophenyl)-5-(3-furyl)-4-oxazolyl]-acetate | + |
| Ethyl 2-[2-(4-fluorophenyl)-5-(3-furyl)-4-oxazolyl]-acetate | + |
| 2-[2-(4-chlorophenyl)-5-(3-furyl)-4-oxazolyl]-acetic acid | + |
| 2-[2-(4-fluorophenyl)-5-(3-furyl)-4-oxazolyl]-acetic acid | + |
| (Positive control) Clofibrate | − |

EXAMPLE 1

37 g of ethyl 3-(4-chlorobenzoylamino)-3-(2-furylcarbonyl)propionate are dissolved in 150 ml of chloroform. 64.9 g of phosphorus oxychloride are added dropwise to the solution at room temperature, and the mixture is refluxed at 60° to 70° C. for 8 hours under stirring. After the reaction is completed, the mixture is poured into ice-water. The aqueous mixture is neutralized with sodium bicarbonate and then extracted with ethyl acetate. The extract is washed with water, dried, treated with activated charcoal and then evaporated under reduced pressure to remove solvent. The residue is crystallized with diisopropyl ether, and then recrystallized from ethanol. 30 g of ethyl 2-[2-(4-chlorophenyl)-5-(2-furyl)-4-oxazolyl]acetate are thereby obtained. Yield: 85.5%

M.p. 105°–106° C.

IR $\gamma_{max}^{nujol}$ (cm$^{-1}$): 1723, 1600.

EXAMPLE 2

1.6 g of ethyl 3-acetylamino-4-(2-furylcarbonyl)propionate, 20 ml of chloroform and 4.8 g of phosphorus oxychloride are treated in the same manner as described in Example 1. The crude product thus obtained is purified by silica gel chromatography (solvent; diisopropyl ether: chloroform = 1:1), whereby 1.2 g of ethyl 2-[2-methyl-5-(2-furyl)-4-oxazolyl]acetate are obtained as an oil. Yield: 80.0%

IR $\gamma_{max}^{film}$ (cm$^{-1}$): 3130, 1735.

EXAMPLE 3

To a solution of 5.0 g of ethyl 3-pentanoylamino-3-(2-furylcarbonyl)propionate in 50 ml of methylene chloride is added a mixture of 10 g of phosphorus pentoxide and 10 g of diatomaceous earth. The mixture is refluxed for 6 hours under stirring. After the reaction is completed, the mixture is treated in the same manner as described in Example 2. 4.0 g of ethyl 2-[2-n-butyl-5-(2-furyl)-4-oxazolyl]acetate are thereby obtained as an oil. Yield: 85.1%

IR $\gamma_{max}^{film}$ (cm$^{-1}$): 3120, 1735.

EXAMPLE 4

To a solution of 10 g of ethyl 3-(4-methoxybenzoylamino)-3-(2-furylcarbonyl)propionate in 60 ml of chloroform are dropwise added 15 ml of thionyl chloride at room temperature. The mixture is refluxed at 60° to 70° C. for 6 hours under stirring. After the reaction is completed, the mixture is treated in the same manner as described in Example 1. 3.0 g of ethyl 2-[2-(4-methoxyphenyl)-5-(2-furyl)-4-oxazolyl]acetate are thereby obtained. Yield: 31.6%

M.p. 64°–66° C.

IR $\gamma_{max}^{nujol}$ (cm$^{-1}$): 3130, 1730.

EXAMPLE 5

4.0 g of ethyl 3-benzoylamino-3-(2-furylcarbonyl)propionate, 20 ml of chloroform and 9.7 g of phosphorus oxychloride are treated in the same manner as described in Example 1. 3.0 g of ethyl 2-[2-phenyl-5-(2-furyl)-4-oxazolyl]acetate are thereby obtained. Yield: 78.9%

M.p. 79°–80° C.

IR $\gamma_{max}^{nujol}$ (cm$^{-1}$): 3130, 1735.

EXAMPLE 6

20 g of ethyl 3-(4-fluorobenzoylamino)-3-(2-furylcarbonyl)propionate, 100 ml of chloroform and 36.8 g of phosphorus oxychloride are treated in the same manner as described in Example 1. 15 g of ethyl 2-[2-(4-fluorophenyl)-5-(2-furyl)-4-oxazolyl]acetate are thereby obtained. Yield: 78.9%

M.p. 110°–111° C.

IR $\gamma_{max}^{nujol}$ (cm$^{-1}$): 3110, 1725.

EXAMPLE 7

10 g of ethyl 3-(4-methylbenzoylamino)-3-(2-furylcarbonyl)propionate, 40 ml of chloroform and 23.3 g of phosphorus oxychloride are treated in the same manner as described in Example 1. 4.0 g of ethyl 2-[2-(4-methylphenyl)-5-(2-furyl)-4-oxazolyl]acetate are thereby obtained. Yield: 42.3%

M.p. 84°–85° C.

IR $\gamma_{max}^{nujol}$ (cm$^{-1}$): 3110, 1725.

EXAMPLE 8

2.0 g of ethyl 3-benzoylamino-3-(3-furylcarbonyl)propionate, 15 ml of chloroform and 4.9 g of phosphorus oxychloride are treated in the same manner as described in Example 1. 1.5 g of ethyl 2-[2-phenyl-5-(3-furyl)-4-oxazolyl]acetate are thereby obtained. Yield: 79.0%

M.p. 84°–85° C.

IR $\gamma_{max}^{nujol}$ (cm$^{-1}$): 3140, 1718.

EXAMPLE 9

8.0 g of ethyl 3-(4-fluorobenzoylamino)-3-(3-furylcarbonyl)propionate, 40 ml of chloroform and 20 g of phosphorus oxychloride are treated in the same manner as described in Example 1. 5.0 g of ethyl 2-[2-(4-fluorophenyl)-5-(3-furyl)-4-oxazolyl]acetate are thereby obtained. Yield: 65.8%

M.p. 102°–103° C.

IR $\gamma_{max}^{nujol}$ (cm$^{-1}$): 3130, 1720, 1643.

EXAMPLE 10

8.5 g of ethyl 3-(4-chlorobenzoylamino)-3-(3-furylcarbonyl)propionate, 50 ml of chloroform and 18.6 g of phosphorus oxychloride are treated in the same manner as described in Example 1. 6.93 g of ethyl 2-[2-(4-chlorophenyl)-5-(3-furyl)-4-oxazolyl]acetate are thereby obtained. Yield: 85.5%

M.p. 124°–125° C.

IR $\gamma_{max}^{nujol}$ (cm$^{-1}$): 3130, 1725.

EXAMPLE 11

12.0 g of ethyl 3-isobutyrylamino-3-(2-furylcarbonyl)propionate, 60 ml of chloroform and 32.7 g of phosphorus oxychloride are treated in the same manner as described in Example 2. 10.0 g of ethyl 2-[2-isopropyl-5-(2-furyl)-4-oxazolyl]acetate are thereby obtained as an oil. Yield: 89.2%

IR $\gamma_{max}^{film}$ (cm$^{-1}$): 3130, 1735.

EXAMPLE 12

5.0 g of ethyl 3-cyclohexylcarbonylamino-3-(2-furylcarbonyl)propionate, 30 ml of chloroform and 16.0 g of phosphorus oxychloride are treated in the same manner as described in Example 2. 3.3 g of ethyl 2-[2-cyclohexyl-5-(2-furyl)-4-oxazolyl]acetate are thereby obtained as an oil. Yield: 70.0%

IR $\gamma_{max}^{film}$ (cm$^{-1}$): 3150, 1740.

EXAMPLE 13

10.0 g of ethyl 3-(3,4-dichlorobenzoylamino)-3-(3-furylcarbonyl)propionate, 50 ml of chloroform and 20.0 g of phosphorus oxychloride are treated in the same manner as described in Example 1. 4.44 g of ethyl 2-[2-(3,4-dichlorophenyl)-5-(3-furyl)-4-oxazolyl]acetate are thereby obtained. Yield: 46.5%

M.p. 130°–131° C.

IR $\gamma_{max}^{nujol}$ (cm$^{-1}$): 1730.

EXAMPLE 14

A solution of 0.4 g of potassium hydroxide in 30 ml of methanol is added to 1.0 g of ethyl 2-[2-(4-chlorophenyl)-5-(2-furyl)-4-oxazolyl]acetate at 5° to 10° C. The mixture is stirred at room temperature for 10 hours. Then, the precipitates are collected by filtration, washed with ether and then dried. 0.85 g of potassium 2-[2-(4-chlorophenyl)-5-(2-furyl)-4-oxazolyl]acetate is obtained. Yield: 80.2%

M.p. >250° C.

IR $\gamma_{max}^{nujol}$ (cm$^{-1}$): 1610.

EXAMPLE 15

0.85 g of potassium 2-[2-(4-chlorophenyl)-5-(2-furyl)-4-oxazoyl]acetate is disoolved in 20 ml of water, and the solution is acidified with hydrochloric acid. The precipitates are collected by filtration and then recrystallized from ethanol. 0.69 g of 2-[2-(4-chlorophenyl)-5-(2-furyl)-4-oxazolyl]acetic acid is thereby obtained. Yield: 90.9%

M.p. 191°–194° C. (decomp.).

IR $\gamma_{max}^{nujol}$ (cm$^{-1}$): 1720.

EXAMPLE 16

3.5 g of ethyl 2-[2-phenyl-5-(2-furyl)-4-oxazolyl]acetate are dissolved in a mixture of 50 ml of methanol and 10 ml of water, and 1.2 g of sodium hydroxide are added thereto. The mixture is stirred at room temperature for 10 hours. After the reaction is completed, the mixture is condensed under reduced pressure to remove methanol. Water is added to the residue, and the aqueous mixture is adjusted to pH 2 with conc. hydrochloric acid, and then extracted with ethyl acetate. The extract is washed with water, dried and then evaporated under reduced pressure to remove solvent. The resdue is recrystallized from ethanol, whereby 2.5 g of 2-[2-phenyl-5-(2-furyl)-4-oxazolyl]acetic acid are obtained. Yield 78.1%

M.p. 175°–177° C.

IR $\gamma_{max}^{nujol}$ (cm$^{-1}$): 3100, 1690.

EXAMPLE 17

5.0 g of ethyl 2-[2-(4-fluorophenyl)-5-(2-furyl)-4-oxazolyl]acetate, 70 ml of methanol, 10 ml of water and 1.5 g of sodium hydroxide are treated in the same manner as described in Example 16. 4.0 g of 2-[2-(4-fluorophenyl)-5-(2-furyl)-4-oxazolyl]acetic acid are thereby obtained. Yield: 87.7%

M.p. 212°–214° C.

IR $\gamma_{max}^{nujol}$ (cm$^{-1}$): 3080, 1700.

EXAMPLE 18

4.0 g of ethyl 2-[2-(4-methylphenyl)-5-(2-furyl)-4-oxazolyl]acetate, 60 ml of methanol, 10 ml of water and 1.5 g of sodium hydroxide are treated in the same manner as described in Example 16. 2.0 g of 2-[2-(4-methylphenyl)-5-(2-furyl)-4-oxazolyl]acetic acid are thereby obtained. Yield: 55.6%

M.p. 176°–177° C.

IR $\gamma_{max}^{nujol}$ (cm$^{-1}$): 3120, 1720.

EXAMPLE 19

2.0 g of ethyl 2-[2-(4-methoxyphenyl)-5-(2-furyl)-4-oxazolyl]acetate, 30 ml of methanol, 3 ml of water and 0.85 g of potassium hydroxide are treated in the same manner as described in Example 16. 1.5 g of 2-[2-(4-methoxyphenyl)-5-(2-furyl)-4-oxazolyl]acetic acid are thereby obtained. Yield: 82.0%

M.p. 177°–178° C.

IR $\gamma_{max}^{nujol}$ (cm$^{-1}$): 3100, 1700.

EXAMPLE 20

1.5 g of ethyl 2-[2-(4-chlorophenyl)-5-(3-furyl)-4-oxazolyl]acetate, 40 ml of methanol, 5 ml of water and 1.5 g of potassium hydroxide are treated in the same manner as described in Example 16. 1.2 g of 2-[2-(4-chlorophenyl)-5-(3-furyl)-4-oxazolyl]acetic acid are thereby obtained. Yield: 87.6%

M.p. 218°–219° C.

IR $\gamma_{max}^{nujol}$ (cm$^{-1}$): 3140, 1715.

EXAMPLE 21

7.0 g of ethyl 2-[2-(3,4-dichlorophenyl)-5-(3-furyl)-4-oxazolyl]acetate, 70 ml of methanol, 7 ml of water and 2.0 g of potassium hydroxide are treated in the same manner as described in Example 16. 5.25 g of 2-[2-(3,4-dichlorophenyl)-5-(3-furyl)-4-oxazolyl]acetic acid are thereby obtained. Yield: 81.0%

M.p. 222°–223° C.

IR$\gamma_{max}^{nujol}$ (cm$^{-1}$): 1725.

EXAMPLE 22

1.1 g of ethyl 2-[2-methyl-5-(2-furyl)-4-oxazolyl]acetate, 20 ml of methanol, 5 ml of water and 0.7 g of potassium hydroxide are treated in the same manner as described in Example 16. 0.55 g of 2-[2-methyl-5-(2-furyl)-4-oxazolyl]acetic acid is obtained. Yield: 56.5%

M.p. 103°–104° C.

IR $\gamma_{max}^{nujol}$ (cm$^{-1}$): 3130, 1720.

EXAMPLE 23

5.0 g of ethyl 2-[2-isopropyl-5-(2-furyl)-4-oxazolyl]acetate, 70 ml of methanol, 7 ml of water and 3.75 g of potassium hydroxide are treated in the same manner as described in Example 16. 3.0 g of 2-[2-isopropyl-5-(2-furyl)-4-oxazolyl]acetic acid are obtained. Yield: 67.1%

M.p. 108°–109° C.

IR $\gamma_{max}^{nujol}$ (cm$^{-1}$): 3110, 1730.

EXAMPLE 24

3.3 g of ethyl 2-[2-cyclohexyl-5-(2-furyl)-4-oxazolyl]acetate, 50 ml of methanol, 5 ml of water and 1.2 g of potassium hydroxide are treated in the same manner as described in Example 16. The crude product is recrystallized from diisopropyl ether, whereby 2.4 g of 2-[2-cyclohexyl-5-(2-furyl)-4-oxazolyl]acetic acid are obtained. Yield: 80%

M.p. 99°–100° C.

IR $\gamma_{max}^{nujol}$ (cm$^{-1}$): 3100, 1730.

EXAMPLE 25

4.0 g of ethyl 2-[2-n-butyl-5-(2-furyl)-4-oxazolyl]acetate, 50 ml of methanol, 5 ml of water and 4.75 g of potassium hydroxide are treated in the same manner as described in Example 16. 3.0 g of 2-[2-n-butyl-5-(2-furyl)-4-oxazolyl]acetic acid are thereby obtained. Yield: 83.3%

M.p. 62°–63° C.

IR $\gamma_{max}^{nujol}$ (cm$^{-1}$): 3100, 1720.

EXAMPLE 26

6.30 g of ethyl 2-[2-(4-fluorophenyl)-5-(3-furyl)-4-oxazolyl]acetate, 70 ml of methanol, 7 ml of water and 1.5 g of sodium hydroxide are treated in the same manner as described in Example 16. 4.88 g of 2-[2-(4-fluorophenyl)-5-(3-furyl)-4-oxazolyl]acetic acid are obtained. Yield: 85%

M.p. 208°–209° C.

IR $\gamma_{max}^{nujol}$ (cm$^{-1}$): 3140, 1710.

EXAMPLE 27

1.0 g of 2-[2-(4-chlorophenyl)-5-(2-furyl)-4-oxazolyl]acetic acid, 1.0 g of 2-chloro-1-methylpyridinium iodide and 0.24 g of isopropanol are dissolved in 30 ml of tetrahydrofuran, and 0.8 g of triethylamine is added dropwise thereto. The mixture is stirred at room temperature for 10 hours. Water is added to the mixture, and the aqueous mixture is evaporated under reduced pressure to remove tetrahydrofuran. The residue is extracted with ethyl acetate, and the extract is washed with an aqueous 20% citric acid solution, an aqueous sodium bicarbonate solution and water, successively. Then, the extract is dried and then evaporated under reduced pressure to remove solvent. The residue is recrystallized from ethanol, whereby 0.5 g of isopropyl 2-[2-(4-chlorophenyl)-5-(2-furyl)-4-oxazolyl]acetate is obtained. Yield: 43.6%

M.p. 96°–97° C.

IR $\gamma_{max}^{nujol}$ (cm$^{-1}$) 3110, 1725.

EXAMPLE 28

2.0 g of 2-[2-(4-chlorophenyl)-5-(2-furyl)-4-oxazolyl]acetic acid, 2.02 g of 2-chloro-1-methylpyridinium iodide, 1.47 g of laurylalcohol, 1.60 g of triethylamine and 60 ml of tetrahydrofuran are treated in the same manner as described in Example 27. 2.4 g of lauryl 2-[2-(4-chlorophenyl)-5-(2-furyl)-4-oxazolyl]acetate are obtained. Yield: 77.4%

M.p. 69.5°–71° C.

IR $\gamma_{max}^{nujol}$ (cm$^{-1}$): 3050, 1735.

EXAMPLE 29

To a solution of 2.0 g of 2-[2-(4-chlorophenyl)-5-(2-furyl)-4-oxazolyl]acetic acid in 20 ml of chloroform are added 2.0 g of thionyl chloride at room temperature. The mixture is refluxed for 3 hours under stirring. After cooling, 0.6 g of n-butanol is added to the mixture, and said mixture is stirred at room temperature for 6 hours. After the reaction is completed, the mixture is evaporated under reduced pressure to remove solvent. The residue is extracted with ethyl acetate, and the extract is washed with an aqueous sodium bicarbonate solution and water, successively. Then, the extract is dried and then evaporated under reduced pressure to remove solvent. The residue is recrystallized from ethanol, whereby 1.5 g of n-butyl 2-[2-(4-chlorophenyl)-5-(2-furyl)-4-oxazolyl]acetate are obtained. Yield: 62.3%

M.p. 96°–97° C.

IR $\gamma_{max}^{nujol}$ (cm$^{-1}$): 3050, 1730.

EXAMPLE 30

To a solution of 1.5 g of 2-[2-(4-chlorophenyl)-5-(2-furyl)-4-oxazolyl]acetic acid and 1.0 g of n-heptyl bromide in 25 ml of dimethylformamide is dropwise added 0.92 g of triethylamine at room temperature. The mixture is stirred at 30° to 40° C. for 4 hours. Then, the mixture is poured into water, and the aqueous mixture is extracted with a mixture of diethyl ether and ethyl acetate (1:1). The extract is treated in the same manner as described in Example 27, whereby 0.85 g of n-heptyl 2-[2-(4-chlorophenyl)-5-(2-furyl)-4-oxazolyl]acetate is obtained. Yield: 42.7%

M.p. 69°–70° C.

IR $\gamma_{max}^{nujol}$ (cm$^{-1}$): 3050, 1735.

PREPARATION 1

(1) To a mixture of 10 g of (2-furylcarbonyl)methylamine hydrochloride, 12.5 g of sodium bicarbonate, 200 ml of ethyl acetate and 100 ml of water are dropwise added 12.0 g of 4-chlorobenzoyl chloride at a temperature below 10° C. under stirring. The mixture is stirred at room temperature for 3 hours. Then, the ethyl acetate layer is collected, washed with water and dried. Said ethyl acetate layer is evaporated under reduced pressure to remove solvent. 16.0 g of N-(4-chlorobenzoyl)-(2-furylcabonyl)methylamine are thereby obtained. Yield: 98.2%

M.p. 138°–139° C.

IR $\gamma_{max}^{nujol}$ (cm$^{-1}$): 3400, 1680, 1660, 1595.

(2) To a solution of 40 g of N-(4-chlorobenzoyl)-(2-furylcarbonyl)methylamine in 160 ml of dimethylformamide are added 7.2 g of 61% sodium hydride at −50° to −40° C. under stirring. The mixture is further stirred at the same temperature for 5 minutes. 27.9 g of ethyl bromoacetate are added to the mixture at −50° to −40° C., and said mixture is stirred at the same temperature for one hour and further stirred at about 0° C. for one hour. After the reaction is completed, the mixture is neutrallized with acetic acid. Then, water is added to the mixture and said mixture is extracted with ethyl acetate. The extract is washed with an aqueous sodium bicarbonate solution and water, successively. Said extract is dried and then evaporated under reduced pressure to remove solvent. The residue is crystallized with a mixture of isopropyl ether and n-hexane, whereby 37.0 g of ethyl 3-(4-chlorobenzoylamino)-3-(2-furylcarbonyl)propionate are obtained. Yield: 70%

M.p. 100°–102° C.

IR $\gamma_{max}^{nujol}$ (cm$^{-1}$): 3300, 3100, 1738, 1680 1630, 1595.

PREPARATION 2

(1) 6.0 g of potassium tert.-butoxide are dissolved in 60 ml of tetrahydrofuran, and 4.4 g of methyl α-isocyanoacetate are added dropwise thereto at −50° C. under stirring. The mixture is stirred at the same temperature for one hour. Then, 5.8 g of 3-furylcarbonyl chloride are added dropwise to the mixture at −50° C. under stirring, and said mixture is further stirred for 2 hours. After the reaction is completed, the mixture is adjusted to a pH of 3 to 4 with acetic acid and then evaporated under reduced pressure to remove solvent. The residue is extracted with ethyl acetate, and the extract is washed with water and an aqueous sodium bicarbonate solution, successively. Said extract is dried and evaporated under reduced pressure to remove solvent. The residue is washed with isopropyl ether, whereby 6.5 g of methyl 5-(3-furyl)oxazole-4-carboxylate are obtained. Yield: 75.4%

M.p. 87°–88° C.

IR $\gamma_{max}^{nujol}$ (cm$^{-1}$): 3120, 1695.

(2) 3 g of methyl 5-(3-furyl)oxazole-4-carboxylate and 2.6 g of 85% potassium hydroxide are dissolved in 100 ml of methanol, and the solution is stirred at room temperature overnight. Then, the reaction mixture is evaporated under reduced pressure to remove solvent, and the residue is acidified with dil. hydrochloric acid. The precipitated crystals are collected by filtration, washed with cold water and then dried. 2.6 g of 5-(3-furyl)oxazole-4-carboxylic acid are thereby obtained. Yield: 93.7%

M.p. 189°–191° C.

IR $\gamma_{max}^{nujol}$ (cm$^{-1}$): 3110, 1700, 1600.

(3) A mixture of 3.0 g of 5-(3-furyl)oxazole-4-carboxylic acid and 50 ml of 3N hydrochloric acid is stirred at 40° to 50° C. for 6.5 hours. Then, the mixture is condensed under reduced pressure, and the residue is crystallized with acetone. The precipitated crystals are collected by filtration, whereby 2.2 g of (3-furylcarbonyl)methylamine hydrochloride are obtained. Yield: 80%

M.p. 196°–198° C.

IR $\gamma_{max}^{nujol}$ (cm$^{-1}$): 3110, 1680, 1560.

(4) 5 g of (3-furylcarbonyl)methylamine hydrochloride, 6.0 g of sodium bicarbonate and 6.0 g of 4-chlorobenzoyl chloride are treated in the same manner as described in Preparation 1-(1). 8.2 g of N-(4-chlorobenzoyl)-(3-furylcarbonyl)methylamine are thereby obtained. Yield: 100%

M.p. 152°–154° C.

IR $\gamma_{max}^{nujol}$ (cm$^{-1}$): 3350, 3110, 1675, 1635, 1595.

(5) 8.3 g of N-(4-chlorobenzoyl)-(3-furylcarbonyl)methylamine, 1.5 g of 61% sodium hydride and 5.8 g of ethyl bromoacetate are treated in the same manner as described in Preparation 1-(2). 8.5 g of ethyl 3-(4-chlorobenzoylamino)-3-(3-furylcarbonyl)propionate are thereby obtained. Yield: 77.3%

M.p. 93°–95° C. (decomp.).

IR $\gamma_{max}^{nujol}$ (cm$^{-1}$): 3340, 3100, 1705, 1670, 1640.

PREPARATION 3

(1) 3.4 g of (2-furylcarbonyl)methylamine hydrochloride, 4.4 g of sodium bicarbonate and 3.3 g of benzoyl chloride are treated in the same manner as described in Preparation 1-(1). 4.0 g of N-benzoyl-(2-furylcarbonyl)methylamine are thereby obtained. Yield: 83.3%

M.p. 132°–133° C.

IR $\gamma_{max}^{nujol}$ (cm$^{-1}$): 3400, 3100, 1675, 1600.

(2) 4.0 g of N-benzoyl-(2-furylcarbonyl)methylamine, 0.8 g of 61% sodium hydride and 3.2 g of ethyl bromoacetate are treated in the same manner as described in Preparation 1-(2). 4.0 g of ethyl 3-benzoylamino-3-(2-furylcarbonyl)propionate are thereby obtained. Yield: 72.7%

M.p. 75°–76° C.

IR $\gamma_{max}^{nujol}$ (cm$^{-1}$): 3300, 1715, 1680, 1640.

PREPARATION 4

(1) 23.4 g of (2-furylcarbonyl)methylamine hydrochloride, 29.3 g of sodium bicarbonate and 23.0 g of 4-fluorobenzoyl chloride are treated in the same manner as described in Preparation 1-(1). 24.0 g of N-(4-fluorobenzoyl)-(2-furylcarbonyl)methylamine are thereby obtained. Yield: 66.8%

M.p. 153°–155° C.

IR $\gamma_{max}^{nujol}$ (cm$^{-1}$): 3410, 3100, 1680, 1655.

(2) 24.0 g of N-(4-fluorobenzoyl)-(2-furylcarbonyl)-methylamine, 4.7 g of 61% sodium hydride and 18.4 g of ethyl bromoacetate are treated in the same manner as described in Preparation 1-(2). 21.0 g of ethyl 3-(4-fluorobenzoylamino)-3-(2-furylcarbonyl)propionate are thereby obtained. Yield: 64.8%

M.p. 95.5°–97° C.

IR $\gamma_{max}^{nujol}$ (cm$^{-1}$): 3300, 1725, 1690, 1640, 1600.

PREPARATION 5

(1) 8.0 g of (2-furylcarbonyl)methylamine hydrochloride, 10.5 g of sodium bicarbonate and 9.2 g of 4-methylbenzoyl chloride are treated in the same manner as described in Preparation 1-(1). 10.0 g of N-(4-methylbenzoyl)-(2-furylcarbonyl)methylamine are thereby obtained. Yield: 83.3%

M.p. 139°–141° C.

IR $\gamma_{max}^{nujol}$ (cm$^{-1}$): 3300, 3140, 1690, 1640.

(2) 12.0 g of N-(4-methylbenzoyl)-(2-furylcarbonyl)-methylamine, 2.3 g of 61% sodium hydride and 9.1 g of ethyl bromoacetate are treated in the same manner as described in Preparation 1-(2). 13.9 g of ethyl 3-(4-methylbenzoylamino)-3-(2-furylcarbonyl)propionate are thereby obtained. Yield: 85.5%

M.p. 83.5°–84.5° C.

IR $\gamma_{max}^{nujol}$ (cm$^{-1}$): 3300, 3250, 1710, 1680, 1640 1610.

PREPARATION 6

(1) 8.0 g of (2-furylcarbonyl)methylamine hydrochloride, 10.5 g of sodium bicarbonate and 10.1 g of 4-methoxybenzoyl chloride are treated in the same manner as described in Preparation 1-(1). 11.0 g of N-(4-methoxybenzoyl)-(2-furylcarbonyl)methylamine are thereby obtained. Yield: 85.3%

M.P. 114°–114° C.

IR $\gamma_{max}^{nujol}$ (cm$^{-1}$): 3310, 3150, 1690, 1635.

(2) 11.0 g of N-(4-methoxybenzoyl)-(2-furylcarbonyl)methylamine, 2.0 g of 61% sodium hydride and 7.8 g of ethyl bromoacetate are treated in the same manner ad described in Preparation 1-(2). 10.7 g of ethyl 3-(4-methoxybenzoylamino)-3-(2-furylcarbonyl)propionate are thereby obtained. Yield: 72.8%

M.p. 104°–106° C.

IR $\gamma_{max}^{nujol}$ (cm$^{-1}$): 3300, 1715, 1680, 1635, 1610.

PREPARATION 7

To a mixture of 3.2 g of (2-furylcarbonyl)methylamine hydrochloride, 10 ml of acetic anhydride and 50 ml of ethyl acetate is dropwise added an aqueous sodium bicarbonate solution at room temperature under stirring until said mixture becomes alkaline. The mixture is further stirred for one hour. Then, the ethyl acetate layer is collected, washed with water, dried and evaporated under reduced pressure to remove solvent. The residue is washed with isopropyl ether, whereby 1.5 g of N-acetyl-(2-furylcarbonyl)methylamine are obtained. Yield: 45.0%

M.p. 114°–115° C.

IR $\gamma_{max}^{nujol}$ (cm$^{-1}$): 3380, 3090, 1670, 1655.

(2) 2.6 g of N-acetyl-(2-furylcarbonyl)methylamine, 0.74 g of 61% sodium hydride and 2.9 g of ethyl bromoacetate are treated in the same manner as described in Preparation 1-(2). 1.6 g of ethyl 3-acetylamino-3-(2-furylcarbonyl)propionate are thereby obtained. Yield: 41%

M.p. 82°–84° C.

IR $\gamma_{max}^{nujol}$ (cm$^{-1}$): 3280, 3100, 1735, 1680, 1650.

PREPARATION 8

(1) 16.0 g of (2-furylcarbonyl)methylamine hydrochloride, 20.5 g of sodium bicarbonate and 11.4 g of isobutyryl chloride are treated in the same manner as described in Preparation 1-(1). 13.0 g of N-isobutyryl-(2-furylcarbonyl)methylamine are thereby obtained. Yield: 67.0%

M.p. 78°–80° C.

IR $\gamma_{max}^{nujol}$ (cm$^{-1}$): 3300, 3130, 1680, 1640.

(2) 13.0 g of N-isobutyryl-(2-furylcarbonyl)methylamine, 3.1 g of 61% sodium hydride and 12.2 g of ethyl bromoacetate are treated in the same manner as described in Preparation 1-(2). 12.0 g of ethyl 3-isobutyrylamino-3-(2-furylcarbonyl)propionate are thereby obtained. Yield: 64.2%

M.p. 65°–67° C.

IR $\gamma_{max}^{nujol}$ (cm$^{-1}$): 3270, 1730, 1660, 1650.

PREPARATION 9

(1) 5.0 g of (2-furylcarbonyl)methylamine hydrochloride, 7.6 g of sodium bicarbonate and 4.8 g of cyclohexylcarbonyl chloride are treated in the same manner as described in Preparation 1-(1). 6.5 g of N-cyclohexylcarbonyl-(2-furylcarbonyl)methylamine are thereby obtained. Yield: 91.5%

M.p. 110°–111° C.

IR $\gamma_{max}^{nujol}$ (cm$^{-1}$): 3250, 3080, 1690, 1640.

(2) 6.5 g of N-cyclohexylcarbonyl-(2-furylcarbonyl)-methylamine, 1.3 g of 61% sodium hydride and 5.1 g of ethyl bromoacetate are treated in the same manner as described in Preparation 1-(2). 5.0 g ethyl 3-cyclohexylcarbonylamino-3-(2-furylcarbonyl)propionate are thereby obtained. Yield: 56.2%

M.p. 58°–61° C.

IR $\gamma_{max}^{KBr}$ (cm$^{-1}$): 3330, 3280, 3120, 1725, 1680, 1640.

PREPARATION 10

(1) 5.0 g of (2-furylcarbonyl)methylamine hydrochloride, 6.6 g of sodium bicarbonate and 4.5 g of n-caproyl chloride are treated in the same manner as described in Preparation 1-(1). 5.0 g of N-n-caproyl-(2-furylcarbonyl)methylamine are thereby obtained. Yield: 77.0%

M.p. 65°–65° C.

IR $\gamma_{max}^{nujol}$ (cm$^{-1}$): 3320, 3100, 1690, 1675, 1630.

(2) 5 g of N-n-caproyl-(2-furylcarbonyl)methylamine, 1.2 g of 61% sodium hydride and 4.4 g of ethyl bromoacetate are treated in the same manner as described in Preparation 1-(2). 5.0 g of ethyl 3-n-caproyl-3-(2-furylcarbonyl)propionate are thereby obtained. Yield: 70.4%

M.p. 50°–51° C.

IR $\gamma_{max}^{KBr}$ (cm$^{-1}$): 3280, 3120, 1740, 1725, 1675, 1640.

PREPARATION 11

(1) 6.0 g of (3-furylcarbonyl)methylamine hydrochloride, 7.8 g of sodium bicarbonate and 6.4 g of 4-fluorobenzoyl chloride are treated in the same manner as described in Preparation 1-(1). 8.5 g of N-(4-fluorobenzoyl)-(3-furylcarbonyl)methylamine are thereby obtained. Yield: 92.4%

M.p. 142°–143° C.

IR $\gamma_{max}^{nujol}$ (cm$^{-1}$): 3370, 3110, 1670, 1640, 1610.

(2) 8.5 g of N-(4-fluorobenzoyl)-(3-furylcarbonyl)methylamine, 1.6 g of 61% sodium hydride and 6.3 g of ethyl bromoacetate are treated in the same manner as described in Preparation 1-(2). 8.0 g of ethyl 3-(4-fluorobenzoylamino)-3-(3-furylcarbonyl)propionate are thereby obtained. Yield: 69.6%

M.p. 107°–109° C. (decomp.).

IR $\gamma_{max}^{KBr}$ (cm$^{-1}$): 3290, 3120, 1725, 1670, 1635.

PREPARATION 12

(1) 6.0 g of (3-furylcarbonyl)methylamine hydrochloride, 7.8 g of sodium bicarbonate and 5.7 g of benzoyl chloride are treated in the same manner as described in Preparation 1-(1). 7.8 g of N-benzoyl-(3-furylcarbonyl)methylamine are thereby obtained. Yield: 91.8%

M.p. 102°–103° C.

IR $\gamma_{max}^{nujol}$ (cm$^{-1}$): 3400, 3100, 1680, 1645, 1610.

(2) 7.8 g of N-benzoyl-(3-furylcarbonyl)methylamine, 1.6 g of 61% sodium hydride and 6.3 g of ethyl bromoacetate are treated in the same manner as described in Preparation 1-(2). 9.2 g of ethyl 3-benzoylamino-3-(3-furylcarbonyl)propionate are thereby obtained. Yield: 86.0%

M.p. 108°–110° C. (decomp.).

IR $\gamma_{max}^{nujol}$ (cm$^{-1}$): 3290, 1725, 1670, 1635.

PREPARATION 13

(1) 5.0 g of (3-furylcarbonyl)methylamine hydrochloride, 6.5 g of sodium bicarbonate and 6.8 g of 3,4-dichlorobenzoyl chloride are treated in the same manner as described in Preparation 1-(1). 7.6 g of N-(3,4-dichlorobenzoyl)-(3-furylcarbonyl)methylamine are thereby obtained. Yield: 82.0%

M.p. 133°–134° C.

IR $\gamma_{max}^{nujol}$ (cm$^{-1}$): 3460, 3360, 3130, 1680, 1650, 1580.

(2) 7.6 g of N-(3,4-dichlorobenzoyl)-(3-furylcarbonyl)methylamine, 1.2 g of 61% sodium hydride and 4.7 g of ethyl bromoacetate are treated in the same manner as described in Preparation 1-(2). 9.0 g of ethyl 3-(3,4-dichlorobenzoylamino)-3-(3-furylcarbonyl)propionate are thereby obtained. Yield: 91.9%

M.p. 127°–129° C. (decomp.).

IR $\gamma_{max}^{nujol}$ (cm$^{-1}$): 3330, 3180, 1715, 1690, 1640, 1590.

What we claim is:

1. A compound of the formula:

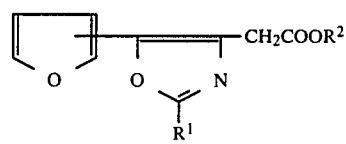

wherein $R^1$ is 4-chlorophenyl or 3,4-dichlorophenyl, and $R^2$ is hydrogen or ethyl, or a pharmaceutically acceptable salt thereof.

2. A compound according to claim 1, wherein $R^1$ is 4-chlorophenyl.

3. A compound according to claim 1, wherein $R^2$ is hydrogen.

4. A pharmaceutically acceptable salt of the compound according to claim 1.

5. A compound according to claim 1, which is ethyl 2-[2-(4-chlorophenyl)-5-(2-furyl)-4-oxazolyl]acetate.

6. A compound according to claim 1, which is ethyl 2-[2-(4-chlorophenyl)-5-(3-furyl)-4-oxazolyl]acetate.

7. A compound according to claim 1, which is 2-[2-(4-chlorophenyl)-5-(2-furyl)-4-oxazolyl]acetic acid or a pharmaceutically acceptable salt thereof.

8. A compound according to claim 1, which is 2-[2-(4-chlorophenyl)-5-(3-furyl)-4-oxazolyl]acetic acid or a pharmaceutically acceptable salt thereof.

9. A compound according to claim 1, which is 2-[2-(3,4-dichlorophenyl)-5-(3-furyl)-4-oxazolyl]acetic acid or a pharmaceutically acceptable salt thereof.

10. A pharmaceutical composition for the treatment of hyperlipidemia which comprises a therapeutically effective amount of a compound according to claim 1 and a pharmaceutically acceptable carrier therefor.

11. The composition of claim 10 suitable for orally administering said compound at a dose of 0.1 to 50 mg per kilogram of body weight per day.

12. The composition of claim 11 suitable for orally administering said compound at a dose of 5 to 20 mg per kilogram of body weight per day.

13. A pharmaceutical composition for the treatment of hyperlipidemia which comprises a therapeutically effective amount of a compound according to claim 12 and a pharmaceutically acceptable carrier therefor.

14. A pharmaceutical composition for the treatment of hyperlipidemia which comprises a therapeutically effective amount of a compound according to claim 13 and a pharmaceutically acceptable carrier therefor.

15. A method for treating hyperlipidemia comprising administering to a host an effective amount of a compound according to claim 14.

16. A method for treating hyperlipidemia comprising administering to a host an effective amount of a compound according to claim 15.

17. A method for treating hyperlipidemia comprising administering to a host an effective amount of a compound according to claim 16.

* * * * *